(12) United States Patent
Turner

(10) Patent No.: US 10,598,540 B2
(45) Date of Patent: *Mar. 24, 2020

(54) HIGH SPEED ROBOTIC WEIGHING SYSTEM

(71) Applicant: VELOX ROBOTICS, LLC, Bainbridge Island, WA (US)

(72) Inventor: Bryan J. Turner, Bainbridge Island, WA (US)

(73) Assignee: VELOX ROBOTICS, LLC, Bainbridge Island, WA (US)

( * ) Notice: Subject to any disclaimer, the term of this patent is extended or adjusted under 35 U.S.C. 154(b) by 266 days.

This patent is subject to a terminal disclaimer.

(21) Appl. No.: 15/855,928

(22) Filed: Dec. 27, 2017

(65) Prior Publication Data

US 2018/0120144 A1 May 3, 2018

Related U.S. Application Data

(63) Continuation of application No. 15/345,302, filed on Nov. 7, 2016, now Pat. No. 9,863,801, which is a continuation-in-part of application No. 14/267,454, filed on May 1, 2014, now Pat. No. 9,564,849.

(60) Provisional application No. 62/251,555, filed on Nov. 5, 2015.

(51) Int. Cl.
| | | |
|---|---|---|
| *G01G 11/00* | (2006.01) |
| *B65G 15/00* | (2006.01) |
| *B65G 39/00* | (2006.01) |
| *G01G 3/16* | (2006.01) |
| *G01N 29/12* | (2006.01) |
| *G01G 19/00* | (2006.01) |
| *H02P 31/00* | (2006.01) |

(52) U.S. Cl.
CPC .......... *G01G 11/003* (2013.01); *B65G 15/00* (2013.01); *B65G 39/00* (2013.01); *G01G 3/16* (2013.01); *G01G 19/005* (2013.01); *G01N 29/12* (2013.01); *H02P 31/00* (2013.01); *B65G 2203/0258* (2013.01); *G01N 2291/028* (2013.01)

(58) Field of Classification Search
CPC ...... G01G 3/16; G01G 11/003; G01G 19/002; G01G 19/005; B65G 15/00; B65G 39/00; B65G 2203/0258; H02P 31/00
See application file for complete search history.

(56) References Cited

U.S. PATENT DOCUMENTS

| | | | | |
|---|---|---|---|---|
| 3,718,031 A | * | 2/1973 | Christmann | G01G 3/16 73/580 |
| 5,393,939 A | * | 2/1995 | Nasuta, Jr. | G01G 11/003 177/145 |
| 5,547,034 A | * | 8/1996 | Wurz | G01G 11/006 177/1 |

(Continued)

*Primary Examiner* — Natalie Huls
(74) *Attorney, Agent, or Firm* — FisherBroyles LLP; Micah D. Stolowitz

(57) ABSTRACT

This disclosure pertains to weighing a physical item while it is moving in a servo-driven conveyor system for e-commerce, logistics, manufacturing and other applications. The introduction of an unknown mass to an electro-mechanical feedback or filter network controlling a conveyance system will modify the steady state behavior of that system in such a way that measuring the phase or frequency shift of an input signal or oscillation will enable us to infer the magnitude of that mass.

23 Claims, 12 Drawing Sheets

Phase Angle

(56) References Cited

U.S. PATENT DOCUMENTS

| | | | | |
|---|---|---|---|---|
| 6,940,025 B1* | 9/2005 | Salomon | ............... | G01G 19/005 |
| | | | | 177/145 |
| 7,096,152 B1* | 8/2006 | Ong | .................... | G01G 19/005 |
| | | | | 117/3 |
| 7,550,681 B2* | 6/2009 | Wang | ....................... | G01G 7/00 |
| | | | | 177/1 |
| 7,820,923 B1* | 10/2010 | Daboub | ................. | G01G 11/12 |
| | | | | 177/1 |
| 2009/0071728 A1* | 3/2009 | Turner | ................. | G01G 19/005 |
| | | | | 177/1 |
| 2009/0216487 A1* | 8/2009 | Streder | ................ | G01G 19/005 |
| | | | | 702/175 |
| 2010/0282521 A1* | 11/2010 | Turner | ................. | G01G 19/005 |
| | | | | 177/1 |
| 2010/0310286 A1* | 12/2010 | Yasumoto | ........... | G03G 15/0131 |
| | | | | 399/302 |
| 2011/0031683 A1* | 2/2011 | Asari | ...................... | B07C 5/165 |
| | | | | 271/264 |
| 2012/0285751 A1* | 11/2012 | Turner | ................. | G01G 19/005 |
| | | | | 177/1 |
| 2014/0327383 A1* | 11/2014 | Turner | ................. | G01G 11/043 |
| | | | | 318/490 |
| 2015/0225179 A1* | 8/2015 | Araki | ..................... | B65G 43/10 |
| | | | | 198/502.1 |

* cited by examiner

Phase Angle

FREQUENCY MODULATION CASE

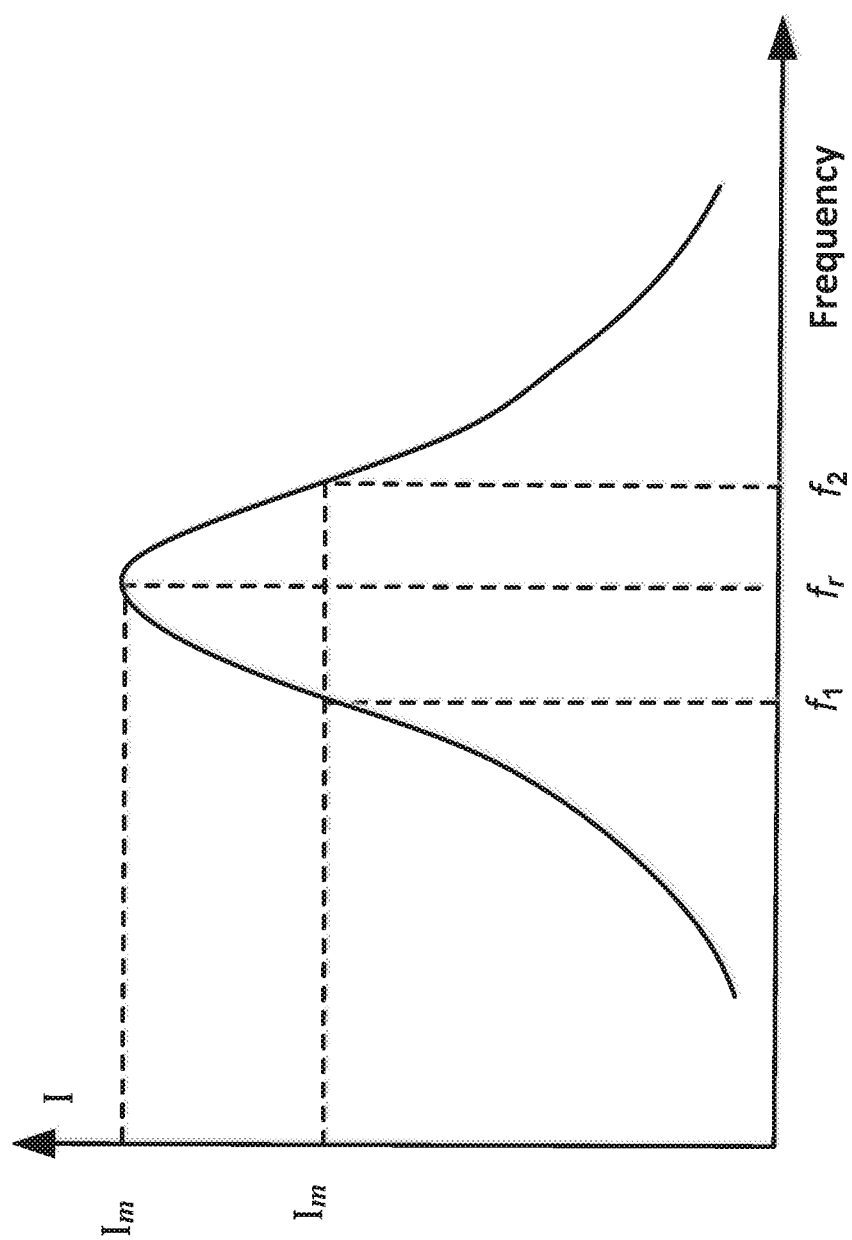

HIGH SPEED ROBOTIC WEIGHING SYSTEM

CROSS-REFERENCE TO RELATED APPLICATIONS

This application is a continuation of application Ser. No. 15/345,302 filed Nov. 7, 2016. The parent application claims benefit under 35 USC § 119 of U.S. Provisional Application No. 62/251,555 filed on Nov. 5, 2015, entitled HIGH SPEED ROBOTIC WEIGHING SYSTEM which is incorporated herein by this reference in its entirety. The parent application also is a continuation-in-part of U.S. application Ser. No. 14/267,454 filed on May 1, 2014, now U.S. Pat. No. 9,564,849, entitled SCALE FOR WEIGHING FLOWING GRANULAR MATERIALS which is incorporated herein by this reference in its entirety.

COPYRIGHT NOTICE

© 2015-2017 Velox Robotics, LLC. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

FIELD OF THE INVENTION

This disclosure pertains to weighing a physical item while it is moving in a servo-driven conveyor system for e-commerce, logistics, manufacturing and other applications.

BACKGROUND OF THE INVENTION

This disclosure pertains to detecting mass, i.e. weighing, a discrete physical item while it is moving. In particular, improvements are disclosed for automated, high-speed, precise weighing of moving objects. The improvements may be implemented in robotic systems and other applications. In our previous work, beginning with U.S. Pat. No. 7,687,727, the primary indicator of mass magnitude is the amplitude of the torque response from the servo system when instructed by a control system to change the speed of a moving item with some unknown mass. The torque signal can be an impulse or a composite of harmonically related sinusoids or other time varying signal. The torque amplitude is tightly correlated with the mass of the moving item and is used to produce a useful measurement of its mass. This is a type of amplitude modulation or AM approach. As with other technologies that rely on amplitude modulation schemes, these torque signals are subject to distortion and noise from a number of sources. In addition, the cited patent applies only to individual discrete items; they must be weighed one at a time. The disclosure that follows solves this and other problems and limitations.

SUMMARY OF THE INVENTION

The following is a summary of the invention in order to provide a basic understanding of some aspects of the invention. This summary is not intended to identify key/critical elements of the invention or to delineate the scope of the invention. Its sole purpose is to present some concepts of the invention in a simplified form as a prelude to the more detailed description that is presented later.

Torque signal noise sources can be suppressed or avoided by utilizing entirely different types of modulation schemes to avoid distortion of measurement. Two of these modulation schemes are phase and frequency modulation, called PM and FM respectively. These modulations types have been used in unrelated contexts such as data communications. We have discovered methods and apparatus to advantageously apply these modulation schemes to the high-speed mass detection problem space.

In one example, a method of weighing a parcel may include the steps of: providing a mechanical conveyor having a drive shaft for moving the parcel; providing a servo motor having a motor shaft for driving the conveyor; coupling the servo motor shaft to the conveyor drive shaft by means of a viscous damper; providing a servo system for driving the servo motor, and arranging the servo system to drive the motor responsive to a time-varying velocity command input signal; providing a motor shaft encoder coupled to the servo motor shaft to generate motor velocity signals; providing a velocity encoder coupled to the conveyor to generate conveyor velocity signals; driving the conveyor responsive to the time-varying velocity command input signal; receiving the parcel onto the moving conveyor; and determining a mass of the parcel based on a phase angle between the motor velocity signals and the conveyor velocity signals.

Additional aspects and advantages of this invention will be apparent from the following detailed description of preferred embodiments, which proceeds with reference to the accompanying drawings.

BRIEF DESCRIPTION OF THE DRAWINGS

FIG. 8 is a graph of an example of a transfer amplitude of a velocity signal vs frequency from the velocity encoder to the servo command input in a system of the type illustrated in FIG. 6.

DETAILED DESCRIPTION OF PREFERRED EMBODIMENTS

Figure 1:
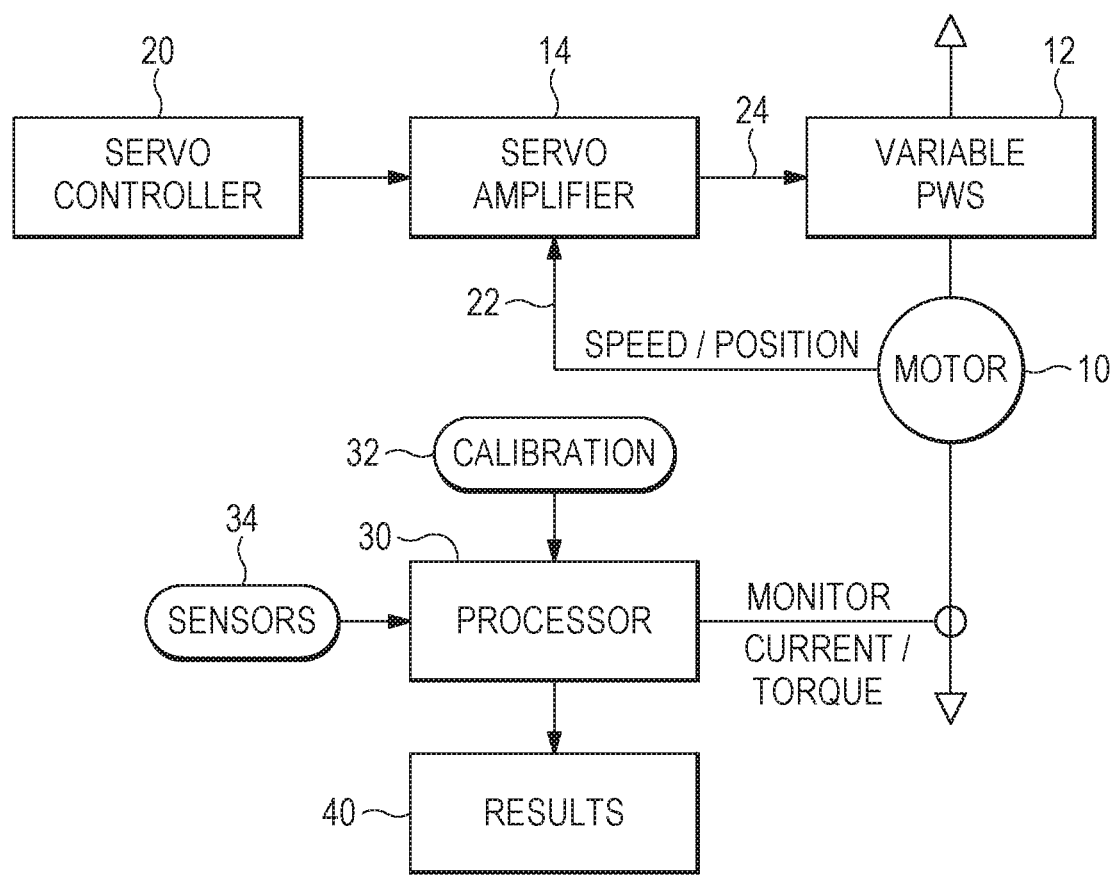
FIG. 1 illustrates a prior art weighing system utilizing motor torque data.

FIG. 1 illustrates a prior art weighing system for mail pieces. In this prior art, the general principle involves subjecting mail pieces to a step function change in velocity created by a servo system, and then monitoring the behavior of the servo (specifically the torque impulse generated) as it compensates for the change in system mass and velocity as a mail piece is introduced. FIG. 1 also illustrates how a digital processor 30 can be provisioned to monitor and process the motor torque information, and compare it to calibration data 32, to generate results 40 representing the mass of a moving mail piece. Sensors 34 may be provided to inform the processor as the moving mail pieces enter and leave a weighing station. This step/impulse model works well in applications where the articles to be weighed are of low mass (typically less than 112 grams) and are moving at high speed (for example, 4 m/s). The prior art is not suitable for weighing larger (heavier) objects such as parcels while they are moving, or weighing granular solids or slurry materials while they are moving.

Figure 2:
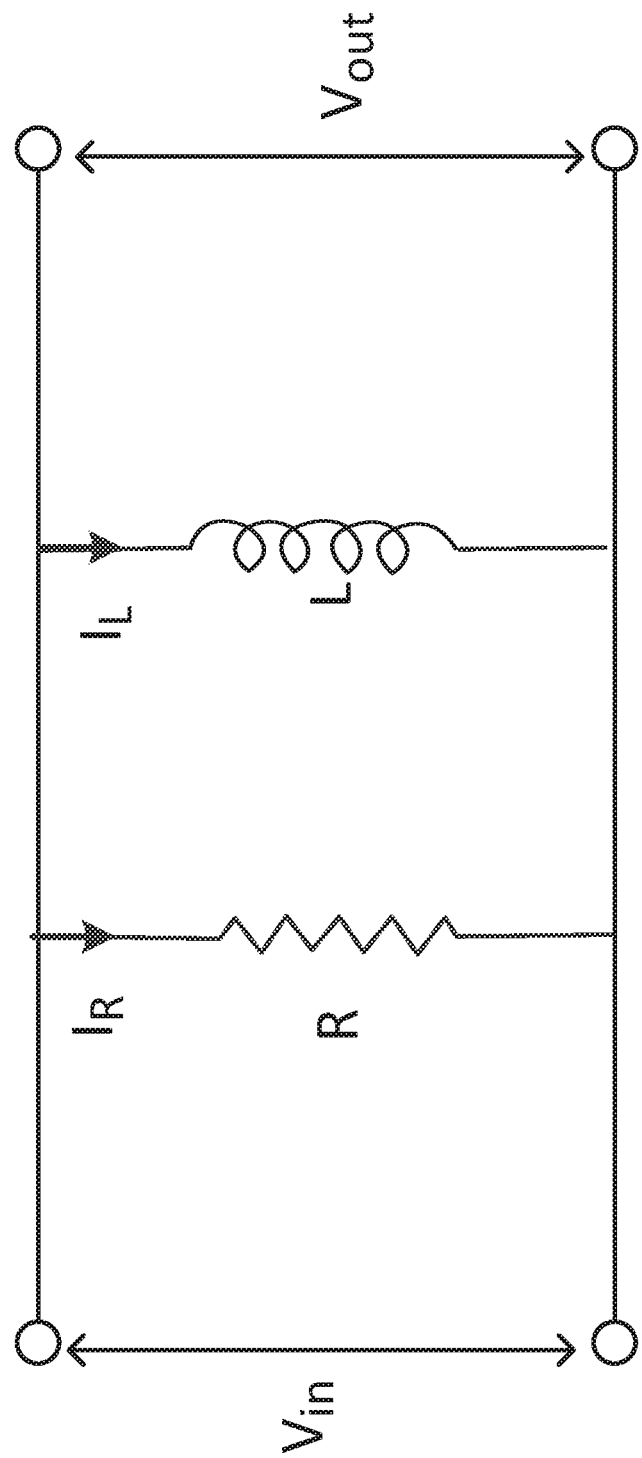
FIG. 2 is an electrical schematic diagram of a parallel RL circuit.

FIG. 2 is an electrical schematic diagram of a parallel RL circuit, showing a variable inductor L as the electrical analog of a mass in a mechanical system. The first case considered is that of phase modulation, a form of angle modulation where a carrier is modulated by an information-carrying signal or reactive parameter variation in a circuit. The realization of this scheme with respect to mass detection involves a motion control system (servo) driving a time varying drive signal e.g. sinusoid into a conveyor system. Note that any time varying signal can be used.

One implementation involves a series mechanical configuration of drive source, viscous damper and mass. An important component of this implementation is the viscous damper and shaft coupler between the servo and the conveyor drive axel. This element is analogous of a resistor in parallel with the inductive (mass) load. This element also connects the two shafts i.e. motor and conveyor drive shaft by way of the damper viscosity. Note that there are implementations analogous to both series and parallel RL circuits. The series mechanical elements are described further below with regard to FIG. 6.

Figure 3:
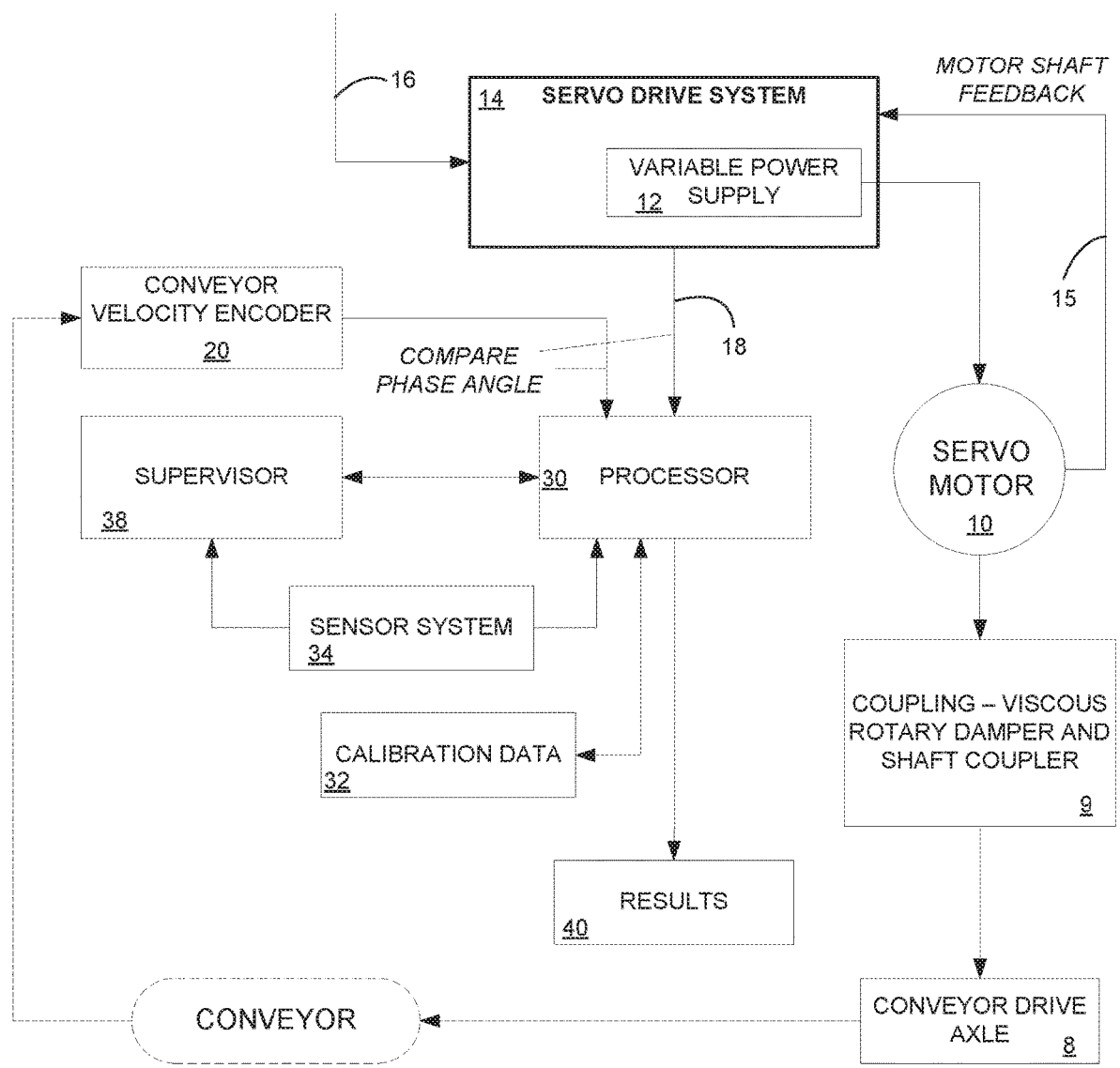
FIG. 3 is a simplified system block diagram illustrating principal control and data signals in one example of a servo-based weighing system.

FIG. 3 is a simplified system block diagram illustrating principal control and data signals in one example of a servo-based weighing system. In FIG. 3, a conveyor has a drive axle 8 that is driven by a servo motor 10. The servo motor 10 shaft is coupled to the conveyor drive axle 8 by a viscous rotary damper and shaft coupler 9. The servo motor is driven by a servo drive system 14. The servo drive system 14 includes a variable power supply 12 to provide drive current to the motor, typically under control of a servo amplifier. The servo drive system 14 drives the motor in response to a command velocity input signal 16. Preferably, the command velocity input signal commands a constant conveyor velocity plus superimposed sinusoidal or other time varying velocity/acceleration signal. The servo drive system compares a motor shaft feedback signal 15 to the input signal 16.

A sensor system 34 may utilize sensors, details of which are known, to monitor, for example, parcels entering and leaving the weighing system. Sensors may also monitor aspects of operation of the scale conveyor. Item detection, or a "start weighing" command, may be generated by a supervisory process or processor 38 in some applications. The command may be based on input from the sensor system 34.

A processor 30, for example, a suitably programmed controller or microprocessor, receives inputs from the sensor system 34, and acts in concert with the supervisor process 38, to carry out weighing operations as detailed below. The processor also has access to stored calibration data 32, which may be stored in memory. The calibration data may be created by utilizing the scale conveyor system to weigh items such as parcels that have a known weight. In an embodiment, the servo drive system is configured to operate at a substantially constant velocity for moving the parcel upon receiving it from an infeed conveyor, and the drive system also superimposes the resulting oscillation signal on that constant velocity.

The processor 30 is coupled to the servo drive system 14 to compare a phase of the servo drive command velocity input signal via 18 to a phase of the output signal to determine a phase difference. The output signal may be based on a velocity encoder 20 coupled to the conveyor. Further, the processor 30 may be configured to compare the phase difference to the stored calibration data to determine a mass of the parcel, and store and/or report the results, block 40.

Figure 4:
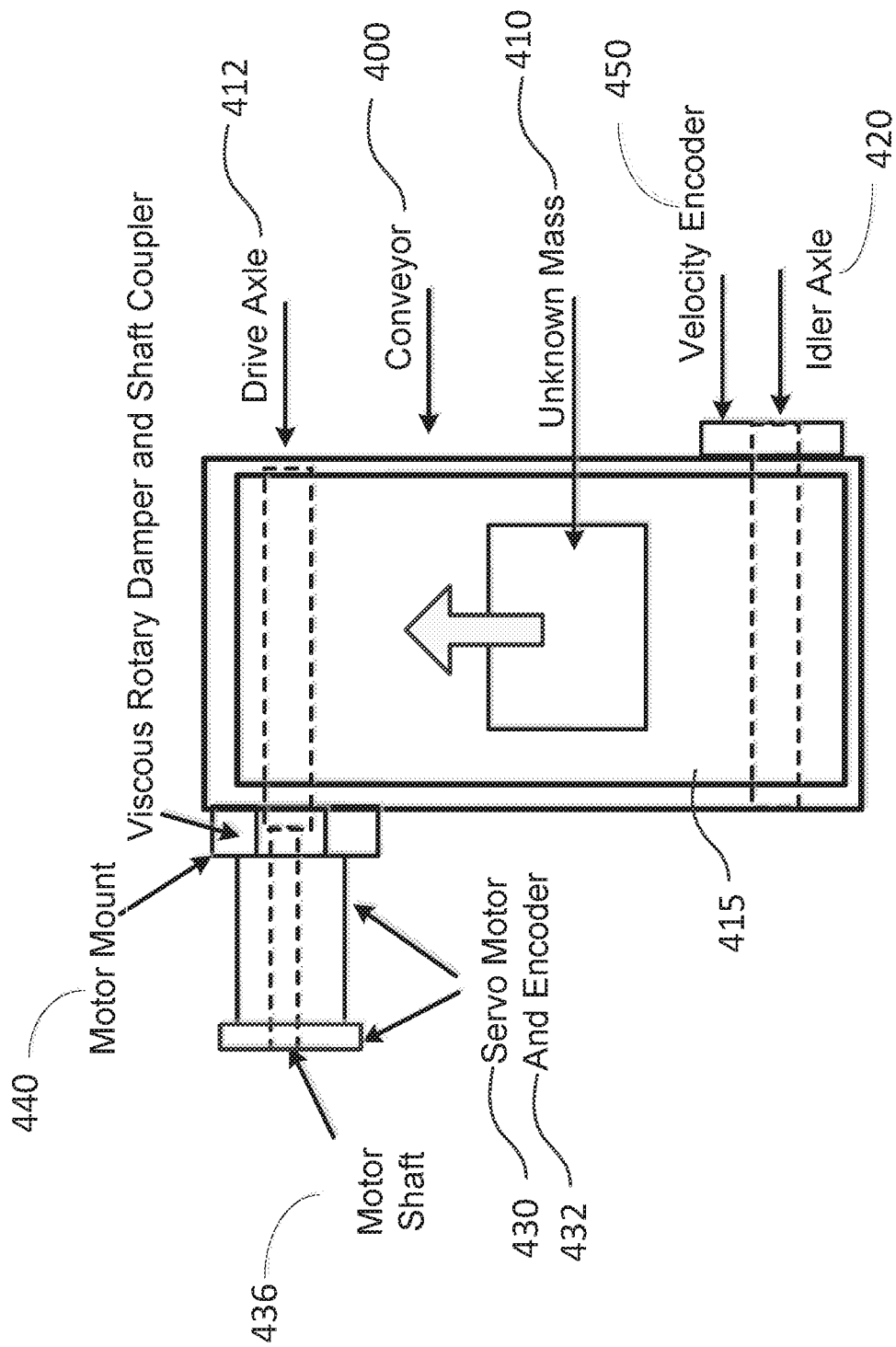
FIG. 4 is a simplified conceptual view of a servo-based conveyor weighing system arranged to exploit velocity signal phase angles to determine mass of an item traveling on the conveyor.

FIG. 4 is a simplified conceptual view of a conveyor weighing system arranged to exploit velocity signal phase difference or phase modulation to determine mass of an item traveling on the conveyor. In operation, as an item with unknown mass passes over the conveyor system, its transfer function will change in a way similar to varying the inductance of a LR network like the one in FIG. 2. A comparison of the drive velocity phase to velocity phase at the output is made. At minimal mass, the phase between these quantities will be close to zero whereas it will be close to 90 degrees when maximal mass is present. Practical systems and methods to exploit these features are further described below.

In FIG. 4, a scale conveyor 400 may be disposed adjacent to an infeed conveyor (See FIGS. 9A and 9B, described below) and arranged to receive a parcel unknown mass 410 from the infeed conveyor. The scale conveyor includes a drive axle 412 and an idler axle 420. The illustration shows use of a conveyor belt 415, but the system may be applied to other conveyors that do not employ a belt. An output velocity encoder 450 captures output velocity signals for use in comparing output velocity phase to the drive velocity phase.

A servo motor 430 having a motor shaft 436 is mounted with a motor mount 440 to drive the drive axle 412 and thus drive the conveyor 400. An encoder 432 is coupled to the motor shaft 436 to provide drive velocity information from which drive velocity phase can be determined for comparison to the output velocity phase detected by encoder 450. The comparison can be conducted by a processor, for example, in an arrangement described with regard to FIG. 3 processor 30, to determine mass of the item 410.

With regard to FIGS. 2 and 4, a parallel electric circuit (FIG. 2) is analogous to a series mechanical circuit. This can be confusing unless one realizes that a velocity measurement at the source servo in a series mechanical circuit is analogous to a current drive measurements in a parallel RL circuit. The phase angle between the velocity vector phases at the servo motor and the velocity encoder 450 will be proportional to the inverse tangent of the ratio of the damper resistance to the mass, in the same way the current phase varies in the parallel LR circuit above. $\Theta = \tan^{-1}(Xd/Xm)$. Xd=impedance of damper, Xm=impedance of mass.

With constant drive frequency and low mass, the velocity phase difference between the drive and the output encoder 450 will trend toward to zero whereas when the mass is large, the phase difference will trend to 90 degrees. When $Xd/2\pi Xm = F$ drive (drive signal frequency), the phase angle between the encoder velocities will be 45 degrees. Xd and F drive should be chosen to produce this corner phase shift at the midpoint of mass range e.g. on a 100 lb scale range, this should be set to produce 45 degrees of phase difference when 50 lbs mass is present.

Frequency Modulation or Frequency Deviation Sensing

Figure 5:
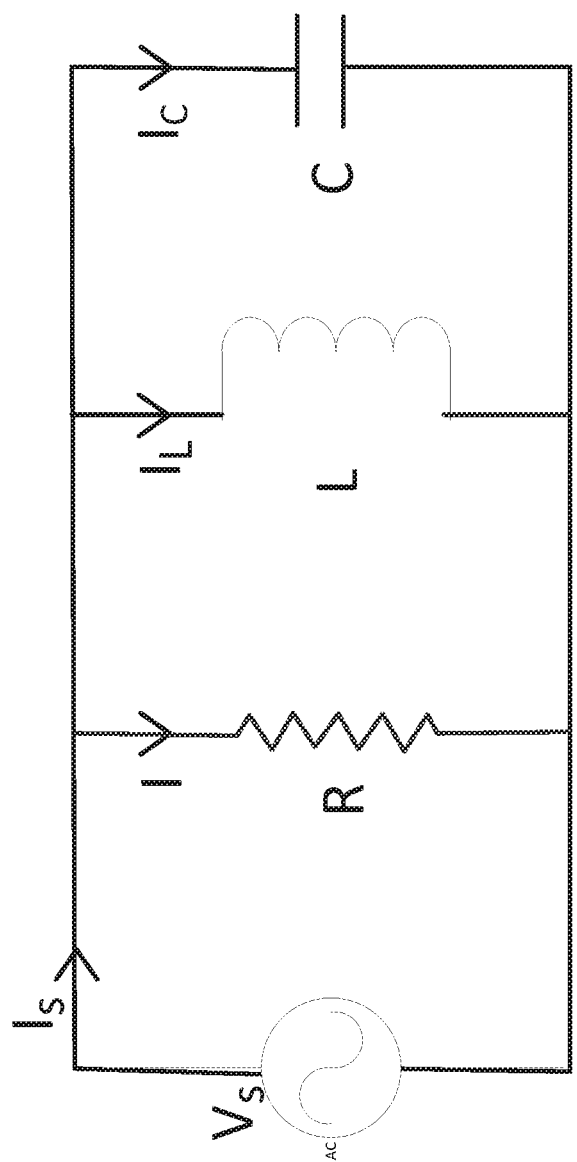
FIG. 5 is an electronic circuit diagram showing a parallel RLC circuit to illustrate analogy to a series mechanical configuration of a drive system (servo system), a rotary spring and damper, shaft coupler and unknown mass corresponding to the inductor L.

FIG. 5 is an electronic circuit diagram showing a parallel RLC feedback circuit to illustrate analogy to a series mechanical configuration of a drive system (servo system), a rotary spring and damper, shaft coupler and unknown mass. This type of circuit will resonate at a frequency dependent on the various components as further explained below. As the resonant frequency is affected by the value of inductor L, analogous to the unknown mass as noted, frequency can be used to determine the unknown mass.

In more detail, as current in the electric circuit is analogous to velocity in the mechanical circuit, attenuation by the reactive elements in the parallel circuit is minimal at the resonant frequency. In this way, the amplitude of the velocity signal from the velocity encoder is maximal at the resonant frequency. This signal is fed back to the servo drive as the velocity command signal. The complete system will oscillate at the resonant frequency until the value of the inductance (mass) changes. Since the conveyor system has nominal mass from the pulleys and belts, the system will oscillate at a frequency associated with an unloaded scale. As an unknown mass is introduced, the oscillation frequency will modulate to the new resonant frequency. The difference between the unloaded frequency and the frequency when the unknown mass is present is measured and is proportional to that mass.

Figure 6:
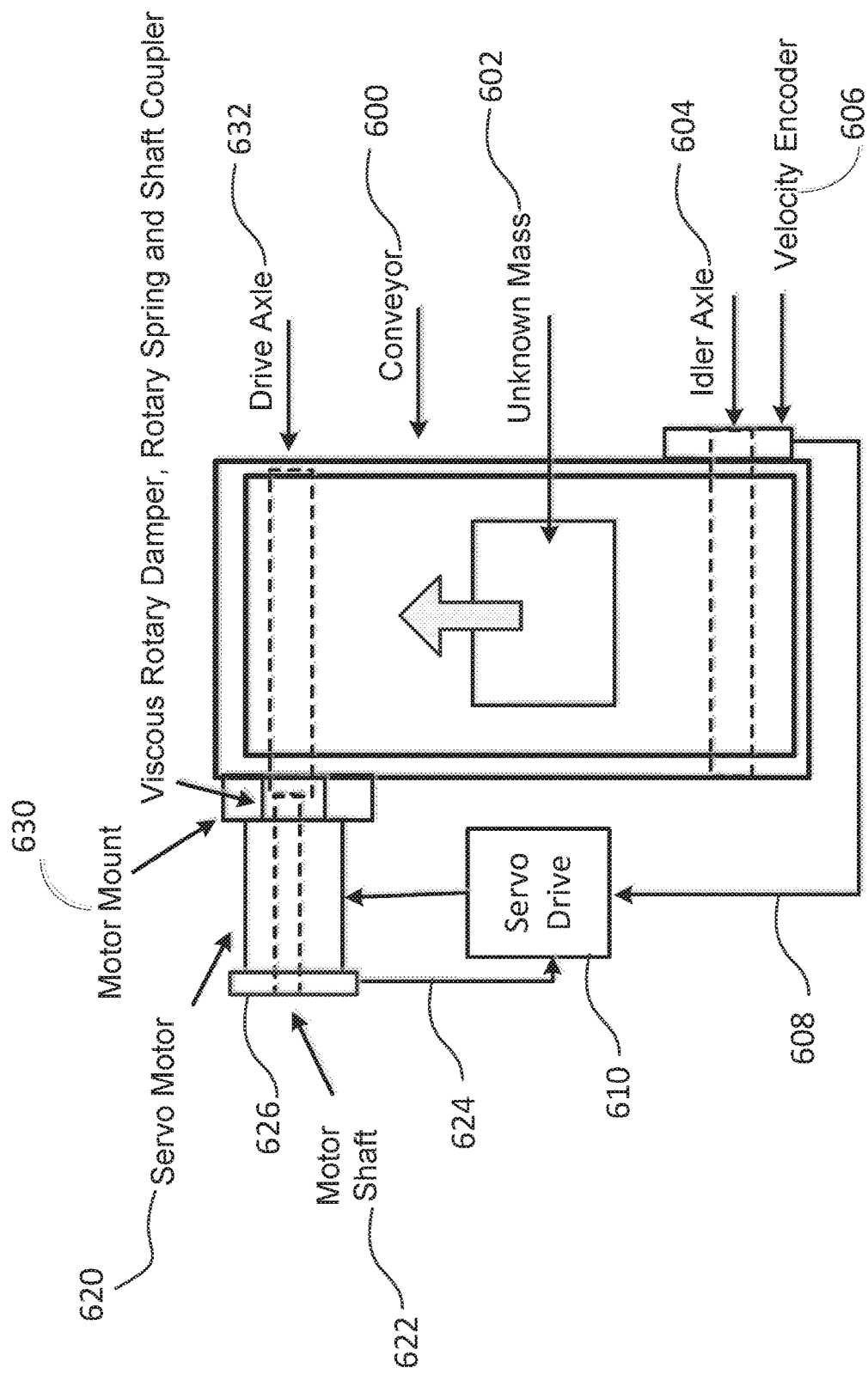
FIG. 6 is a simplified system block diagram illustrating principal control and data signals in an example of a servo-based weighing system, in which changes in resonant frequencies of the system are utilized to determine an unknown mass of an item introduced on the conveyor.
Figure 9A:
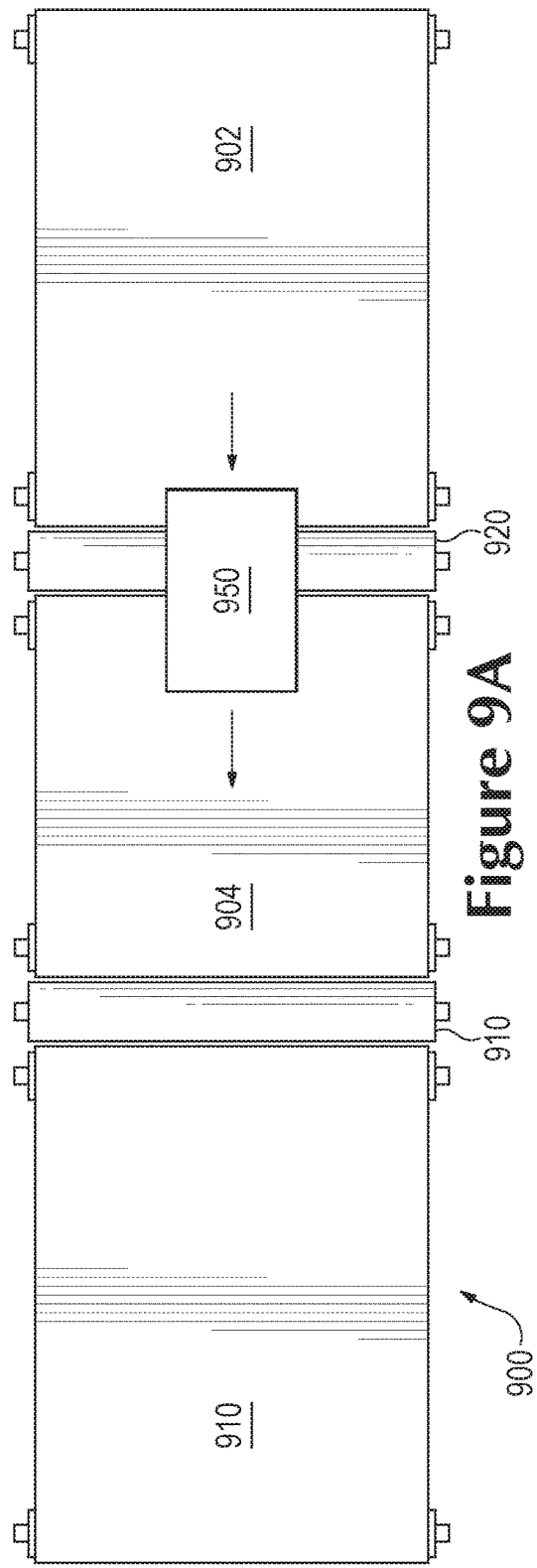
FIG. 9A is a top view of a mechanical conveyor system that may be used in some embodiments of the weighing systems and methods disclosed herein.

FIG. 6 is a simplified system block diagram illustrating principal control and data signals in an example of a servo-based weighing system, in which changes in resonant frequencies of the system are utilized to determine an unknown mass of an item introduced on the conveyor. Here, a conveyor 600 is driven by a drive axle 632. The conveyor may be a belt type conveyor. There may be infeed and or outfeed systems adjacent to the conveyor 600 (not shown) for material handling, for example, as illustrated in FIG. 9A, described below. A servo drive system 610 (for example, a servo amplifier and servo controller) is arranged to drive a servo motor 620. The servo motor shaft 622 is coupled to the conveyor drive axle 632 to drive the conveyor. The motor is controlled via feedback loop 624 which may be coupled, for example, to an encoder 626 arranged to monitor the motor shaft.

The servo motor 620 is coupled to the drive axle 632 by a motor mount 630 and a viscous rotary damper, rotary spring and shaft coupler. The viscous damper, the rotary spring, conveyor and unknown mass comprise the feedback network. The velocity signal from the velocity encoder 606 is fed into the command velocity input of the servo drive 610 via path 608. This configuration represents a positive feedback loop supporting natural self-exciting oscillation. The servo drive system is configured to operate at a constant velocity as a conveyor but to also superimpose the resulting oscillation signal on that constant velocity.

Figure 7:
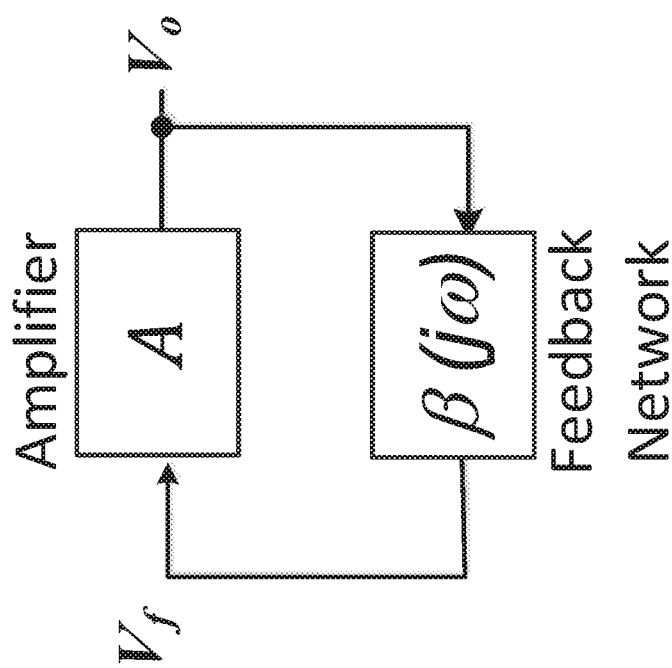
FIG. 7 shows a conceptual circuit diagram illustrating a closed loop feedback network.

FIG. 7 shows a conceptual circuit diagram illustrating a closed loop feedback network. As applied to the present context, the viscous damper, the rotary spring, conveyor and unknown mass comprise the feedback network β. The velocity signal $V_f$ from the velocity encoder is fed into the command velocity input of the servo drive A. This configuration represents a positive feedback loop supporting natural self-exciting oscillation. The servo drive system is configured to operate at a constant velocity as a conveyor but to also superimpose the resulting oscillation signal on that constant velocity.

Example Implementation

One example of a servo motor that may be used in some embodiments is Kollmorgen Model number C042A. A suitable servo Servo drive is Kollmorgen, Model No. AKD-B00606. These products are commercially available from Kollmorgen USA located at 203A West Rock Road, Radford VA 24141.

The following example of an embodiment of a scale is merely illustrative and not intended to be limiting.
In-feed conveyor speed: 2 m/s
Min/Max parcel length: 100/1500 mm
Max parcel weight: 50 kg
Required resolution: +/−100 g
Velocity differential: +/−0.5 m/s
Total scale length: 1900 mm
Example Servo Specification:
Max sustained torque: 10 Nm (For weighing purposes only. Suggest 100% over sizing for nominal torque required to spin mechanism)
Torque loop resolution: 16 bits
Torque loop sample rate: 2000 samples/s
RPM range 2400-4800.

FIG. 8 is a graph of an example of a transfer amplitude of a velocity signal vs frequency from the velocity encoder 606 to the servo command input 608 in a system of the type illustrated in FIG. 6. In general, for such configurations, the natural resonant frequency is given by $f=\frac{1}{2\pi}\sqrt{(LC)}$ where L is the analog of the variable mass and C is the analog of the inverse of the rotary spring constant.

Figure 9B:
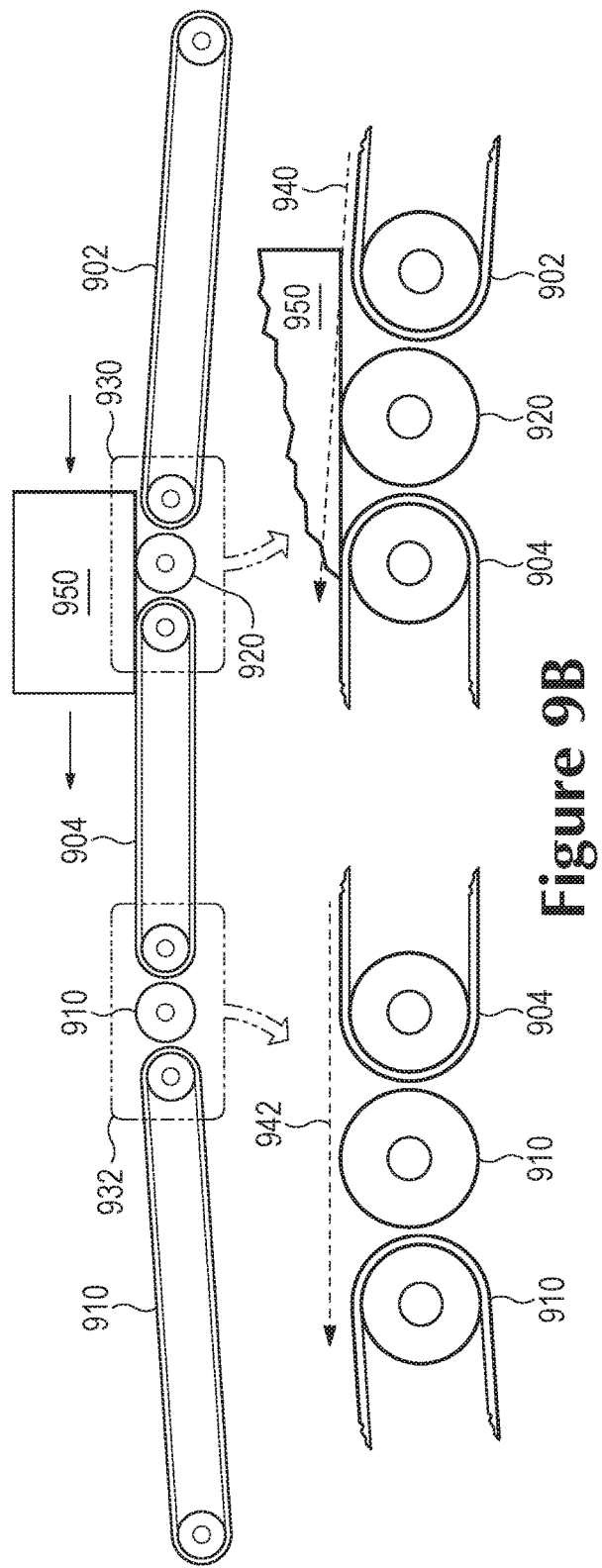
FIG. 9B is a side elevational and exploded view of the conveyor system of FIG. 9A.

FIG. 9A is a simplified top view of a mechanical conveyor system 900 that may be used in some embodiments of the weighing systems and methods disclosed herein. Here, the system 900 includes an infeed conveyor 902, a weighing or scale conveyor 604 and an outfeed conveyor 910. A sample parcel 950 is shown moving from 902 to 904. Only one parcel is shown for simplicity, however, an advantage of the present innovations is the ability to weigh parcels individually even though there may be more than one parcel on the scale, and the parcels may be overlapping on the scale. FIG. 9B is a side elevation view of the system of FIG. 9A. In FIG. 9B, regions 930 and 932 are shown below in exploded views to provide more detail. As indicated by dashed line 940, as the parcel 950 leaves the infeed conveyor 902 it rides over the isolation roller 920 keeping the leading end initially spaced above the weighing conveyor 904. Then, as it moves further (from right to left in the figure), the parcel will drop onto the weighing conveyor 904. As and when the leading edge falls onto the weighing conveyor, the parcel is still supported by the isolation roller 920 but it is off of the infeed 902. In some embodiments, the isolation roller is positioned so as to isolate the parcel as it moves from the infeed conveyor to the scale conveyor so that the parcel rests on only one of the infeed conveyor and the scale conveyor at a given time. When there are multiple, possibly overlapping parcels (discussed below), the isolation roller keeps the multiple parcels resting on only one of the infeed conveyor and the scale conveyor at a given time.

On the outfeed side, refer to dashed line 942, indicated to illustrate a similar arrangement to isolate the weighing conveyor from the outfeed conveyor 910. The isolation rollers are idler rollers; that is, they are unpowered and rotate with very low resistance, so they do not contribute to accelerating a parcel and thus do not affect the servo-driven weighing operations in any material way.

Figure 10:
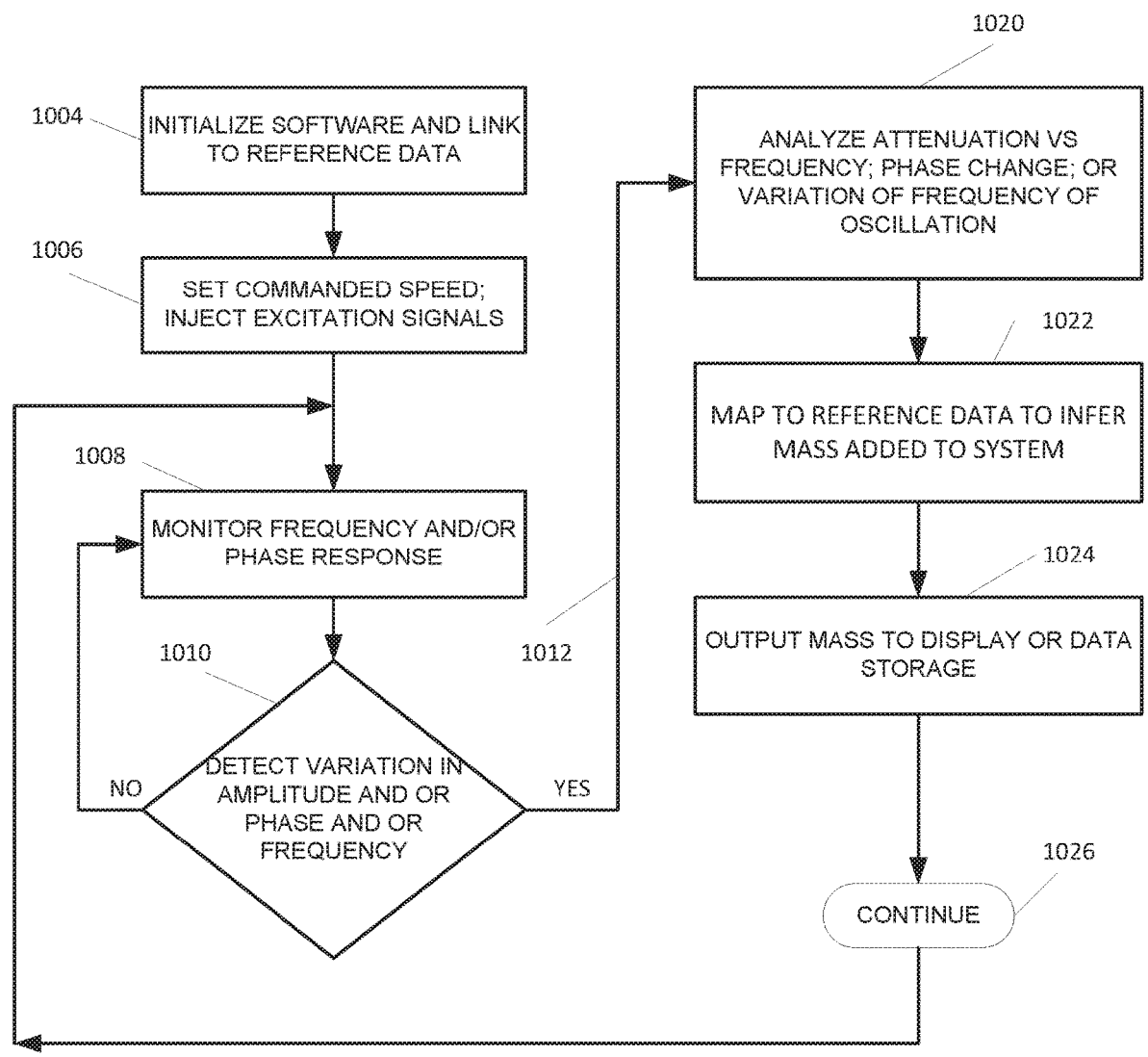
FIG. 10 is a simplified flow diagram of a process for weighing a moving item utilizing one or more of amplitude, frequency and phase modulation of servo feedback signals.

FIG. 10 is a simplified, general flow diagram of a process for weighing a moving item utilizing one or more of amplitude, frequency shift and phase angle modulation of servo feedback signals. At block 1004, control software is initialized and it may be linked to reference data or calibration data. Control software may provide the calculations necessary for measuring parcel mass as explained above. In an embodiment, the software may execute on a processor such as processor 30 shown in FIG. 3. A commanded speed is set for controlling the servo system. The commanded speed may be a time-varying signal. It may be a sinusoidal signal as explained in some examples above. It is also referred to as a velocity command input signal. At block 1006, excitation signals may be injected to cause the servo loop to oscillate. In an embodiment, the servo loop may naturally self-oscillate in view of the feedback loop from a conveyor velocity encoder as described with regard to FIG. 6. In operation, block 1008, a system monitors frequency and or phase response as described above.

At decision block 1010, a system may detect variation in amplitude and or phase and or frequency, in other words, any combination of one or more of these metrics can be used. If no change is detected, for example, while no parcel is being weighed, the logic loops back to block 1008 to continue monitoring. When a change is detected, the logic flows to block 1020 to analyze attenuation vs. frequency; phase change; or variation of oscillation as explained in more detail above. The resulting change or changes at then mapped to reference data (or calibration data) to infer the mass of an item (for example, a parcel or any other item) added to the system, block 1022. The results may be output to a display and or data storage, block 1024. In an embodiment, the results may be input to an inventory or shipping system or other software for e-commerce, logistics, manufacturing and other applications, especially those where weighing moving objects "on the fly" may provide considerable improvements in throughput and cost reduction. After output block 1024, the logic loops back via 1026 to resume monitoring for changes, block 1008, and so on, continuously.

The weighing operations may be conducted on a weigh conveyor 904 as described with regard to FIGS. 9A and 9B. There is no requirement that a parcel move off of the conveyor, for example, to an outfeed conveyor 910, before another parcel lands on the weigh conveyor 904 to be weighed. The arrival of the second parcel will cause the perturbations discussed above, from which its mass may be inferred, notwithstanding the presence of another parcel (which typically has already been weighed). In some cases, the parcels may be overlapping in location along the conveyor.

Figure 11:
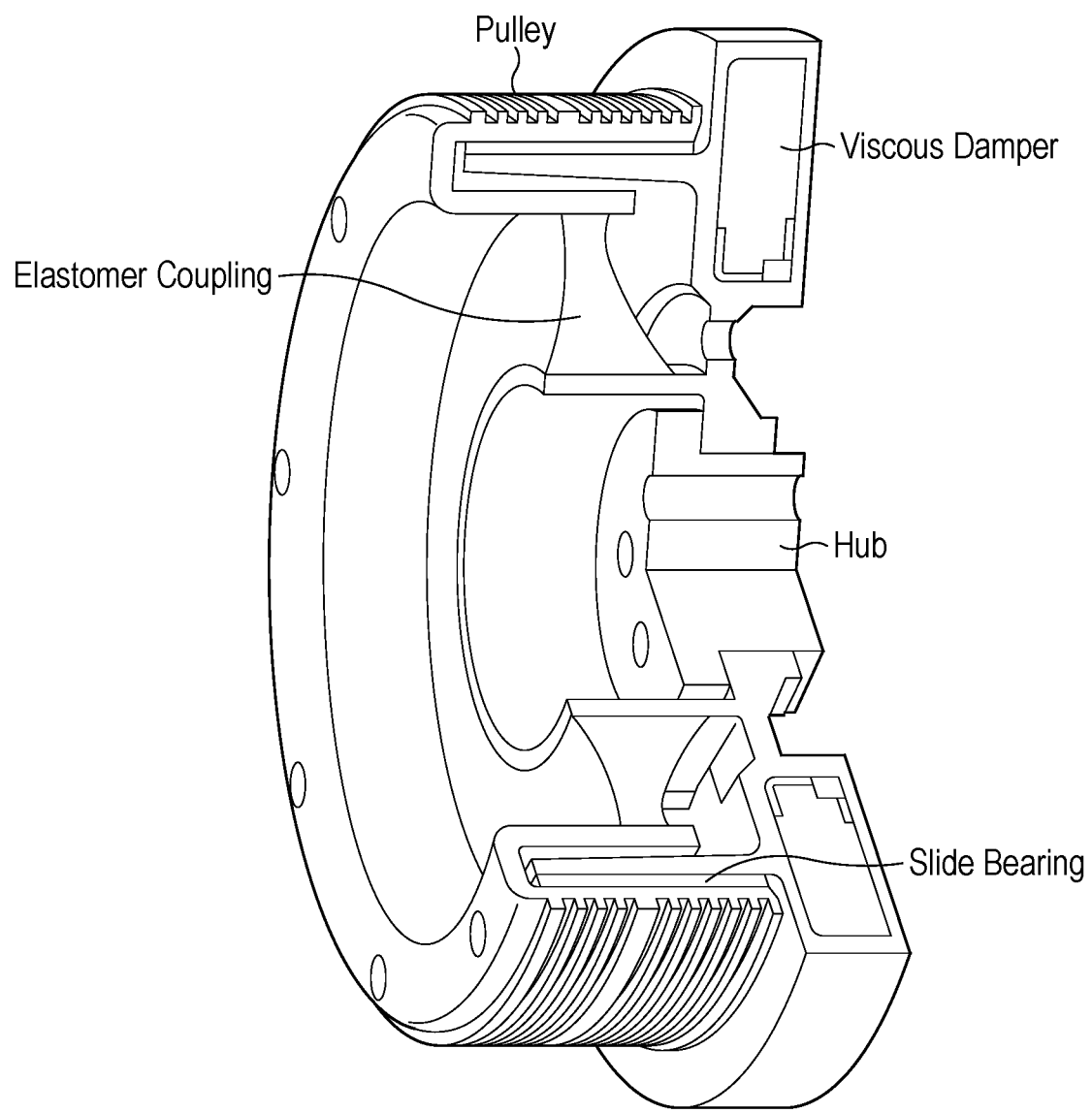
FIG. 11 is a cutaway perspective view of one example of a viscous damper element of a type that may be used in some embodiments to couple the servo to a conveyor drive axle.

FIG. 11 is a cutaway perspective view of one example of a viscous damper element of a type that may be used in some embodiments to couple the servo to a conveyor drive axle. Such elements are commercially available, for example, from Hasse & Wrede of the Knorr-Bremse AG group in Germany.

Figure 12:
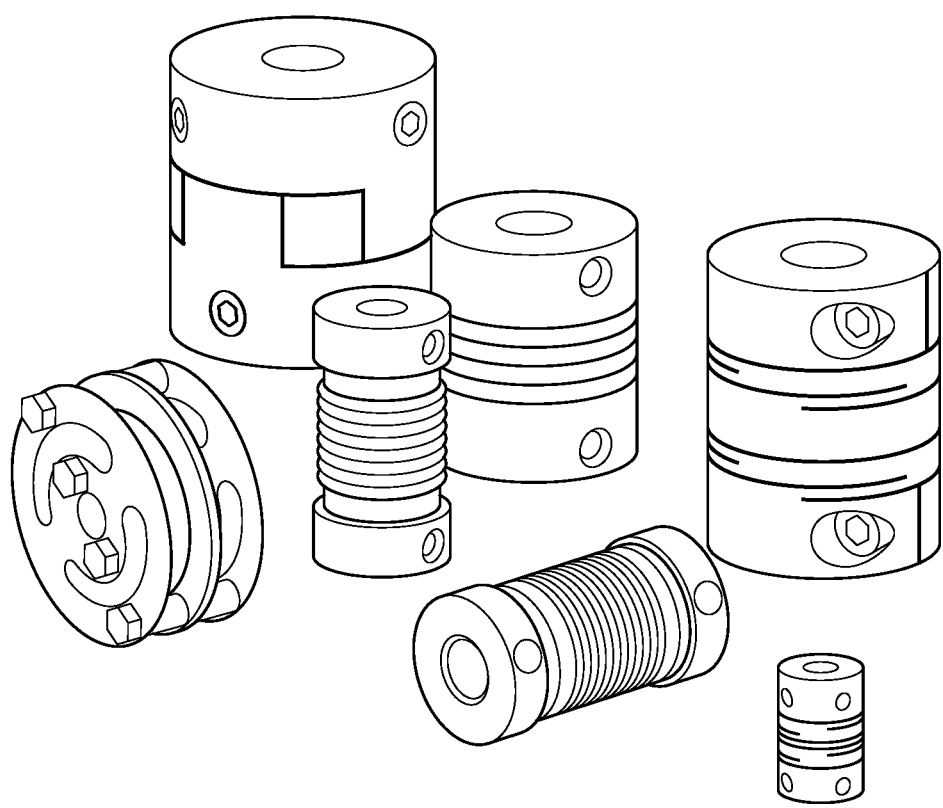
FIG. 12 shows some examples of rotary springs that may be used in some embodiments.

A rotary spring such as part number RFSXK-3019-10-08 from reliance couplers provides the torsional stiffness required for resonance. FIG. 12 shows some examples of rotary springs that may be used in some embodiments.

Processors, Software and Memory

Most of the equipment discussed above comprises mechanical assemblies, processing hardware coupled to the mechanical assemblies, and associated software. For example, the typical electronic device may include one or more processors and software executable on those processors to carry out the operations described. We use the term software herein in its commonly understood sense to refer to programs or routines (subroutines, objects, plug-ins, etc.), as well as data, usable by a machine or processor. As is well known, computer programs generally comprise instructions that are stored in machine-readable or computer-readable storage media. Some embodiments of the present invention may include executable programs or instructions that are stored in machine-readable or computer-readable storage media, such as a digital memory. We do not imply that a "computer" in the conventional sense is required in any particular embodiment. For example, various processors, embedded or otherwise, may be used in equipment such as the components described herein.

Memory for storing software again is well known. In some embodiments, memory associated with a given processor may be stored in the same physical device as the processor ("on-board" memory); for example, RAM or FLASH memory disposed within an integrated circuit microprocessor or the like. In other examples, the memory comprises an independent device, such as an external disk drive, storage array, or portable FLASH key fob. In such cases, the memory becomes "associated" with the digital processor when the two are operatively coupled together, or in communication with each other, for example by an I/O port, network connection, etc. such that the processor can read a file stored on the memory. Associated memory may be "read only" by design (ROM) or by virtue of permission settings, or not. Other examples include but are not limited to WORM, EPROM, EEPROM, FLASH, etc. Those technologies often are implemented in solid state semiconductor devices. Other memories may comprise moving parts, such as a conventional rotating disk drive. All such memories are "machine readable" or "computer-readable" and may be used to store executable instructions for implementing the functions described herein.

A "software product" refers to a memory device in which a series of executable instructions are stored in a machine-readable form so that a suitable machine or processor, with appropriate access to the software product, can execute the instructions to carry out a process implemented by the instructions. Software products are sometimes used to distribute software. Any type of machine-readable memory, including without limitation those summarized above, may be used to make a software product. That said, it is also known that software can be distributed via electronic transmission ("download"), in which case there typically will be a corresponding software product at the transmitting end of the transmission, or the receiving end, or both.

Having described and illustrated the principles of the invention in a preferred embodiment thereof, it should be apparent that the invention may be modified in arrangement and detail without departing from such principles. We claim all modifications and variations coming within the spirit and scope of the following claims.

The invention claimed is:

1. A system for weighing items while they are moving, the system comprising:
a scale conveyor arranged to receive at least one item from an infeed conveyor, the scale conveyor including a drive axle;
a servo motor having a shaft;
a servo drive system coupled to the server motor to drive the motor responsive to a command velocity input signal;
a motor mount arranged for coupling the servo motor shaft to the drive axle of the scale conveyor, the motor mount comprising a viscous rotary damper, a rotary spring and a shaft coupler, arranged to connect the servo motor shaft to the drive axle applying the rotary damper viscosity;
a velocity encoder coupled to the scale conveyor to generate velocity signals responsive to a current velocity of the scale conveyor; and
a processor configured to—
monitor at least one of (a) a frequency of oscillation and (b) a phase response of the velocity signals to detect a variation;
responsive to detecting the variation, analyze the variation of frequency of oscillation and or the phase response; and
infer a mass of the item(s) received on the scale conveyor based on the analysis.

2. The system of claim 1 wherein:
a frequency of oscillation before the item is received on the conveyor is a natural resonant frequency arising based on the velocity signals from the velocity encoder being fed back to the servo drive system as the command velocity input of the servo drive system so as to provide a positive feedback loop supporting natural self-exciting oscillation; and
the variation is detected by comparing the frequency of oscillation before the item is received on the conveyor to the frequency of oscillation after the item is received on the conveyor.

3. The system of claim 1 wherein the phase response is determined by a phase difference between the servo drive system input command signal and the velocity signals generated by the velocity encoder.

4. The system of claim 1 wherein the command velocity input signal comprises a time varying command velocity input signal.

5. The system of claim 1 wherein the time varying command velocity input signal is a substantially sinusoidal signal.

6. The system of claim 5 wherein the time varying command velocity input signal has a frequency on the order of 10 Hz.

7. The system of claim 1 including an isolation roller disposed in between the infeed conveyor and the scale conveyor, the isolation roller positioned so as to isolate the item as it moves from the infeed conveyor to the scale conveyor so that the item rests on only one of the infeed conveyor and the scale conveyor at a given time.

8. The system of claim 7 wherein the scale conveyor has a surface that defines a scale deck height that is parallel to a top surface of the isolation roller.

9. The system of claim 7 and further comprising a second isolation roller disposed in between the scale conveyor and outfeed conveyor, the second isolation roller positioned so as to isolate an item moving from the scale conveyor to the outfeed conveyor so that the item is supported by only one of the scale conveyor and the outfeed conveyor at a given time.

10. A method of weighing an item comprising the steps of:
providing a mechanical conveyor having a drive shaft for moving the item;
providing a servo motor having a motor shaft for driving the conveyor;
coupling the servo motor shaft to the conveyor drive shaft by means of a viscous damper;
providing a servo system for driving the servo motor, and arranging the servo system to drive the motor responsive to a time-varying velocity command input signal;
providing a motor shaft encoder coupled to the servo motor shaft to generate motor velocity signals;
providing a velocity encoder coupled to the conveyor to generate conveyor velocity signals;
driving the conveyor responsive to the time-varying velocity command input signal;
receiving first item onto the moving conveyor; and
determining a mass of the first item based on a phase angle between the motor velocity signals and the conveyor velocity signals.

11. The method of claim 10 further comprising:
receiving a second item onto the moving conveyor while the first item is still on the moving conveyor;
after receiving the second item, measuring a phase angle between the motor velocity signals and the conveyor velocity signals; and
determining a mass of the second item based on the measured phase angle.

12. The method of claim 11 wherein the second item overlaps the first item in location along the conveyor.

13. The method of claim 11 including:
inputting a substantially sinusoidal signal as the time-varying velocity command input signal, the sinusoidal signal having a frequency F on the order of 10 Hz.

14. The method of claim 10 including:
estimating an impedance of the viscous damper based on the time-varying velocity command input signal; and
calculating the mass of the first item based on the phase angle being proportional to an inverse tangent function of a ratio of the viscous damper impedance to an impedance Xm of the item mass.

15. The method of claim 11 including:
calculating the item mass based on a relationship $Xd/2\pi Xm = F$ drive, wherein Xd is an impedance of the viscous damper at the frequency F drive.

16. The method of claim 15 including:
selecting a desired range of mass for weighing items; and
selecting Xd and F drive to produce a 45-degree phase shift at a midpoint of the desired mass range.

17. The method of claim 16 wherein the desired range is approximately 0 to 100 pounds, thereby producing 45 degrees of phase angle between the motor velocity signals and the conveyor velocity signals when an item of 50 pounds mass is present.

18. A method of weighing a moving item comprising the steps of:
providing a mechanical conveyor having a drive shaft for moving an item;
providing a servo motor having a motor shaft for driving the conveyor;
coupling the servo motor shaft to the conveyor drive shaft by means of a viscous damper and a rotary spring;

providing a servo system for driving the servo motor, and arranging the servo system to drive the motor responsive to a velocity command input signal, the input signal selected to drive the motor at a predetermined nominal constant velocity;

acquiring conveyor velocity signals responsive to motion of the conveyor;

superimposing the conveyor velocity signals on to the velocity command input signal to so as to form a positive feedback loop that supports natural self-exciting oscillation, the feedback loop including a feedback network comprising the viscous damper, the rotary spring, and the conveyor, so that the feedback loop oscillates at a natural resonant frequency of the feedback network while the conveyor is unloaded;

measuring the resonant frequency while the conveyor is unloaded;

receiving a first item onto the moving conveyor; and determining a mass of the first item based on measuring a change in the resonant frequency relative to the resonant frequency measured while the conveyor was unloaded.

19. The method of claim 18 including:

storing calibration data that associates oscillation frequency to mass of an item; and determining the mass of the first item based on the calibration data.

20. The method of claim 18 including:

estimating the natural resonant frequency by $f=1/(2\pi\sqrt{(LC)})$ where L is the analog of the variable mass of the first item and C is the analog of the inverse of the rotary spring constant; and selecting the rotary spring constant to produce a desired natural resonant frequency on the order of 10 Hz.

21. The method of claim 18 including:

receiving a second item onto the moving conveyor while the first item is still on the moving conveyor; and determining a mass of the second item based on measuring a change in the resonant frequency relative to the resonant frequency measured before the second item arrived on the conveyor.

22. The method of claim 21 wherein the second item overlaps the first item in location along the conveyor.

23. The method of claim 18 including:

receiving a stream of additional items onto the conveyor, and determining a mass per unit time of the additional items based on measuring changes in the resonant frequency relative to the resonant frequency measured before the additional items began arriving on the conveyor.

\* \* \* \* \*